United States Patent
Gossler et al.

(10) Patent No.: US 10,092,213 B2
(45) Date of Patent: Oct. 9, 2018

(54) METHOD AND ARRANGEMENT FOR COMPUTER-ASSISTED REPRESENTATION AND/OR EVALUATION OF MEDICAL EXAMINATION DATA

(75) Inventors: Thomas Gossler, Erlangen (DE); Martin Huber, Uttenreuth (DE); Nadine Liebs, Erlangen (DE); Michael Rusitska, Erlangen (DE); Marcus Thäle, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/561,364

(22) Filed: Jul. 30, 2012

(65) Prior Publication Data
US 2013/0035957 A1    Feb. 7, 2013

(30) Foreign Application Priority Data

Aug. 2, 2011   (DE) ................... 10 2011 080 260

(51) Int. Cl.
*G06F 3/048*   (2013.01)
*A61B 5/055*   (2006.01)
(Continued)

(52) U.S. Cl.
CPC ............ *A61B 5/055* (2013.01); *G06F 19/321* (2013.01); *G16H 50/50* (2018.01); *A61B 5/743* (2013.01);
(Continued)

(58) Field of Classification Search
CPC ...... G06F 19/321; G06F 19/322; G06F 17/30; G06F 19/30; G06F 19/32; G06F 19/324;
(Continued)

(56) References Cited

U.S. PATENT DOCUMENTS 5,987,345 A * 11/1999 Engelmann ........... G06F 19/321
                                                       128/920
6,785,410 B2   8/2004 Vining et al.
(Continued)

FOREIGN PATENT DOCUMENTS

CN         1666710 A      9/2005
DE    102005050000 A1     4/2006
(Continued)

OTHER PUBLICATIONS

Google patents search, Aug. 12, 2014.*
(Continued)

*Primary Examiner* — Tran N Nguyen
(74) *Attorney, Agent, or Firm* — Harness, Dickey & Pierce, P.L.C.

(57) ABSTRACT

Computer-assisted structuring of medical examination data and/or one or more examination data records is disclosed. A method of at least one embodiment includes providing at least one medical examination data record, which includes patient-specific data described textually and/or symbolically and/or at least one image data record created with the aid of a radiological examination device; providing at least one body model image, which represents a body model matching the examination data; and registering the at least one examination data record with the body model, wherein at least one position in the body model is assigned to the examination data record; the position being made known for interaction by way of a user interface.

20 Claims, 6 Drawing Sheets

(51) Int. Cl.
- *G06F 19/00* (2018.01)
- *G16H 50/50* (2018.01)
- *G06F 3/0482* (2013.01)
- *G06F 3/0481* (2013.01)
- *A61B 6/00* (2006.01)
- *A61B 8/00* (2006.01)
- *A61B 5/00* (2006.01)
- *G16H 10/60* (2018.01)

(52) U.S. Cl.
CPC .............. *A61B 5/7435* (2013.01); *A61B 6/463* (2013.01); *A61B 8/463* (2013.01); *G06F 3/04812* (2013.01); *G16H 10/60* (2018.01)

(58) Field of Classification Search
CPC .... G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 50/24; G06Q 50/22; G06Q 40/08; G06Q 10/10; A61B 5/1128; A61B 19/5244; H04L 29/0809; G06T 7/0012; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/40; G16H 70/60; G16H 80/00
USPC ............. 705/3; 348/162; 382/103, 224, 128; 600/407; 715/738
See application file for complete search history.

(56) References Cited

U.S. PATENT DOCUMENTS

| | | | |
|---|---|---|---|
| 7,155,043 B2* | 12/2006 | Daw | G01R 33/56 128/920 |
| 7,634,733 B2* | 12/2009 | Sadikali | G06F 19/321 715/738 |
| 7,949,167 B2 | 5/2011 | Krishnan et al. | |
| 7,979,383 B2* | 7/2011 | Heilbrunn et al. | 707/792 |
| 8,295,438 B2* | 10/2012 | Harada et al. | 378/98.2 |
| 9,075,907 B2* | 7/2015 | Fujimoto | |
| 2004/0068170 A1* | 4/2004 | Wang | A61B 6/463 600/407 |
| 2005/0148852 A1 | 7/2005 | Tank | |
| 2006/0078195 A1 | 4/2006 | Vaillant et al. | |
| 2006/0173858 A1* | 8/2006 | Cantlin et al. | 707/10 |
| 2009/0244352 A1 | 10/2009 | Harada | |
| 2010/0080434 A1 | 4/2010 | Seifert et al. | |
| 2010/0310141 A1 | 12/2010 | Wilson | |
| 2011/0125526 A1* | 5/2011 | Gustafson | G06F 19/321 705/3 |
| 2011/0235887 A1 | 9/2011 | Bertsch et al. | |
| 2012/0014559 A1 | 1/2012 | Suehling et al. | |
| 2013/0038738 A1* | 2/2013 | Ando et al. | 348/162 |

FOREIGN PATENT DOCUMENTS

| | | |
|---|---|---|
| DE | 102005037374 A1 | 2/2007 |
| DE | 102010012797 A1 | 9/2011 |
| WO | WO-03046810 A1 | 6/2003 |
| WO | WO-2010081094 A2 | 7/2010 |
| WO | WO 2011066486 A2 | 6/2011 |

OTHER PUBLICATIONS

Google patents search, Sep. 22, 2015.*
Google patents search, Feb. 17, 2016.*
WO 2012049851 A1, Zaiki et al.*
Google patents search, May 9, 2016.*
German Search Report for German Application No. 102011080260.6 dated May 29, 2012.
Priority Document German Application No. 102011080260.6 filed Aug. 2, 2011.
Chinese Office Action and English translation thereof dated Apr. 26, 2016.
Chinese Office Action and English translation thereof dated Feb. 5, 2018.

* cited by examiner

METHOD AND ARRANGEMENT FOR COMPUTER-ASSISTED REPRESENTATION AND/OR EVALUATION OF MEDICAL EXAMINATION DATA

PRIORITY STATEMENT

The present application hereby claims priority under 35 U.S.C. § 119 to German patent application number DE 10 2011080260.6 filed Aug. 2, 2011, the entire contents of which are hereby incorporated herein by reference.

FIELD

At least one embodiment of the invention generally focuses on the fields of medical engineering and medical information technology and generally relates to computer-assisted structuring of medical examination data and/or one or more examination data records.

BACKGROUND

The main application area is based inter alia on the field of radiology, in which computer-assisted RIS (Radiology Information System), HIS (Hospital Information System) and PACS (Picture Archiving and Communication system") are conventionally used. The diagnosis is based on a medical imaging examination on different modalities, such as for instance a computed tomograph (CT), a magnetic resonance tomograph (MRT), a positron emission tomograph (PET), an x-ray device (x-ray) or an ultrasound device (US). The cited radiological examination devices provide the image data record. The image data record is generally an image volume data record, which contains a volume image, or an image series data record, which contains a series of images.

Image data records are created by way of modern imaging methods, such as for instance computed tomography (CT), magnetic resonance (MR) or ultrasound (US), the contents of which are so complex that a comprehensive and fault-free evaluation by way of radiologists is only possible with difficulty.

These imaging methods can generate very detailed and versatile data relating to patients on account of improved resolution or new examination protocols and methods. A large part of this data is nowadays quantitative in imaging diagnostics and can, such as for instance laboratory values, contribute to assessing the development of illnesses. At the same time, physicians are to present this abundance of data in a clear manner.

Current systems in most cases inadequately satisfy this requirement, since data from different imaging methods cannot be represented together or because the physician must consider individual preexaminations sequentially and/or must read the assigned textual diagnosis. To preserve an overview of an individual imaging study, it may pose a challenge if one considers that studies increasingly include a large number of individual images.

The evaluation of the image data records largely takes place in a computer-assisted fashion at diagnostic stations, which provide for observation and navigation through the image data record and a summary of the evaluation (for instance as text or dictation). The image data record is to this end stored in series of medical images, which a radiologist essentially observes sequentially, wherein he/she dictates the evaluation. In particular, the appearance, position and changes to pathological structures are described in the evaluation. The pathological structures are for instance tumors, but also vessels, bones etc. which feature a pathological deviation compared with a healthy normal state.

Before a radiologist currently starts with the diagnosis of medical images, he/she will, if available, firstly read the previous diagnosis of a patient and if applicable consider the associated image data. He/she herewith navigates, guided by the diagnosis text (e.g. "mass lesion in the 6th liver segment", "fracture of the 7th rib, left") in an image diagnosis software (e.g. PACS, DICOM Viewer, Advanced Visualization) to the described individual diagnoses. He/she subsequently diagnoses the current image data systematically, wherein his/her cognitive output consists in reaching a coherent clinical picture and thus a diagnosis from numerous pathological changes and abnormalities. Both the individual image diagnosis (pathological abnormalities, often extended by measurements of tumor sizes and degrees of stenosis) and also the summarized evaluation are subsequently verbalized in the form of a radiological examination report and forwarded to the treating physician for instance.

More recent software for image diagnosis facilities the physician with navigation in terms of individual image diagnosis, by these usually being shown in the form of a list and by selecting an individual diagnosis, directly representing the corresponding images in a form suited to representing the individual diagnosis. A qualitative graphic visualization of diagnoses is possible for specific medical diagnosis procedures. This is however specific and does not allow for a uniform and at the same time flexible visualization of the diagnoses throughout all diagnosis procedures.

Modern software for image diagnosis also enables the simultaneous representation of several image data records (adjacent to one another or superimposed). The image data records can herewith also originate from different imaging methods. Registration of the image data records herewith enables individual image diagnoses to be compared longitudinally or observed in extended representations (e.g. anatomical details by means of CT, functional information by means of MR, metabolic information by way of PET).

Aside from the cognitive output already mentioned above, which has to adduce the radiologist to a coherent clinical picture and/or diagnosis when combining numerous individual diagnoses (possibly from different sources), a further mental stress on the radiologist resides in him/her permanently switching between different types of information representation. Even if the relevant individual image diagnoses are collected within the image diagnosis software at a central point in the form of a list, the radiologist must consequently switch between a verbal representation of a diagnosis and its visual representation. The same problem results in turn on the part of the referring physician. These have to read, and for their part interpret, the information collected in the examination report using different types of information representation in order to obtain an informed understanding of the overall clinical picture.

SUMMARY

An embodiment of the present invention improves on the afore-cited information representation of the afore-cited examination and/or diagnosis data, which may include textual descriptions and image data records.

A method and an apparatus as well as a computer program product according to the independent claims are disclosed. Advantageous embodiments of the invention form the subject matter of the dependent claims or can be inferred from the subsequent description as well as from the example embodiments.

An interactive whole body model is used for the diagnosis of medical data of a patient. The entire quantity of medical data relating to a patient examination is registered with the body model. With the subsequent diagnosis, the full context information relating to each individual diagnosis is therefore available at any time.

The results of previous patient examinations are also registered with the same body model on this basis, so that changes to the diagnoses can be shown between different points in time (also animated as film). Registration of the results of different examinations on a body model also enables reference to be made to possible inconsistencies in the results.

With the aid of the semantic annotations which were generated within the scope of the registration and possibly preceding diagnosis and which render the medical significance of a diagnosis and/or an anatomical or pathological structure comprehensible to a computer, it is possible to intelligently navigate between the whole body model and the original image data.

In this way, a uniform type of information representation is enabled at any time and in any procedural context across all body regions, organs and image data records of different modalities. As a result, learning and synergy effects and higher efficiencies result during the further (development) and use of the system.

A further aspect of an embodiment of the invention is an arrangement, preferably one or several servers and/or computers, for computer-assisted structuring of medical examination data comprising means and/or modules for implementing the afore-cited method, which can be defined in a hardware and/or software relevant fashion and/or as a computer program product.

The patient examination data and/or diagnosis data can be shown here on a display apparatus.

BRIEF DESCRIPTION OF THE DRAWINGS

Further advantages, details and developments of the invention result from the subsequent description of exemplary embodiments in conjunction with the drawings, in which.

Figure 1:
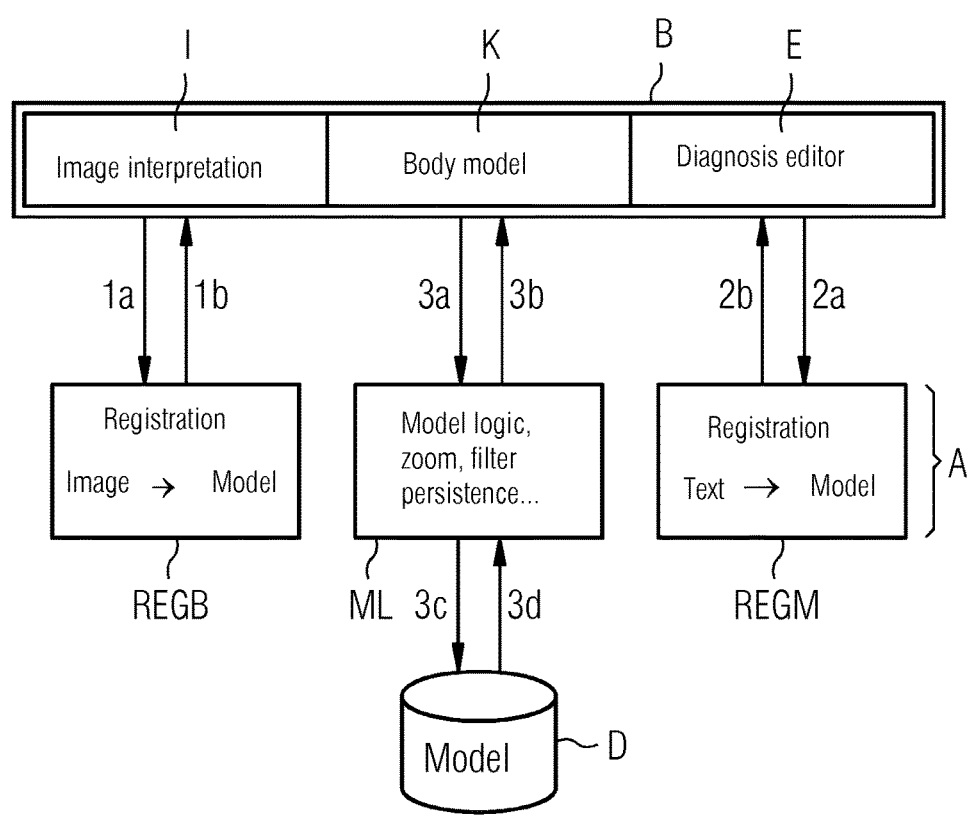
FIG. 1 shows an overview of an embodiment of the method and/or system.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an example embodiment of the invention in the form of an architecture of a software or hardware implementation. A user interface B for instance in the form of a diagnostic station enables a user, in particular a radiologist, to access image data records which are stored in a database for data management purposes D. The possibilities of visualizing, image interpretation I and editing E of medical images as well as diagnosis are available to the user at the diagnostic station by means of dictation or text entry. This diagnostic station is extended such that it also indicates the said body model K and enables the user to interact inter alia as in the interactions shown in FIGS. 2 to 6. Image diagnoses are transmitted largely fully automatically into the body model, wherein different methods and/or algorithms A and/or services are used, which can be roughly classified as follows:

Automatic image analysis method. A plurality of algorithms for detecting lung, abdominal or chest lesions exists on the one hand. On the other hand, methods based on mechanical learning are used to "parse" the images, which is known for instance from US 2010/0080434 A1 "Hierarchical Parsing and Semantic Navigation Of Full Body Computed Tomography Data", the entire contents of which are hereby incorporated herein by reference; and to learn clinical pictures, which is known for instance from U.S. Pat. No. 7,949,167 B2 "Automatic Learning Of Image Features to Predict Disease", the entire contents of which are hereby incorporated herein by reference.

Semiautomatic method for image analysis. In this case the user "accepts", possibly according to a manual correction, the results of automatic image analysis methods. The user in these cases often also extends the automatically determined information relating to image diagnosis by further characteristics and interpretations ("moderate stenosis", "infiltrating"). DE 10 2010 012 797.3 "System zur Effizienzsteigerung und Strukturierung radiologischer Befundung" [System for efficiently increasing and structuring radiological diagnosis], the entire contents of which are hereby incorporated herein by reference, already proposed methods for semiautomatic diagnosis.

The user manually creates the image diagnoses by implementing measurements and evaluations (e.g. length, surface, volume, average density etc.) in the images. In these cases, the position of the image diagnosis is known, since it is found directly in the image. The position in the image (volume) can therefore take place by way of classical registration algorithms REGB (see 1a, 1b). In the simplest case, a registration takes place for instance with the model based on automatically detected field markers. To this end, proximately automatically detected field markers are initially determined for the image diagnosis and the relative position with respect to these field markers is transmitted to the body model. An already proposed registration method is described in U.S. 61/294,256 "Semantics-Driven Image Registration", the entire contents of which are hereby incorporated herein by reference. In addition, the user will also use the possibility of writing or dictating image diagnoses directly into the diagnosis without specific measurements or evaluations. If the diagnoses are prestructured (e.g. in separate sections for head, neck/shoulder, thorax, abdomen/pelvis), this structure can be used to determine the anatomical position of individual image diagnoses. If this is not possible, the anatomical position of individual image diagnoses can generally be determined by means of text analysis REGM. If the anatomical position is determined, a (purely semantic) registration can likewise take place on the body model 2a, 2b. The interaction with the body model K consists inter alia of zooming and filtering the body model. The assistance for the user interaction such as also the function for charging and storing the models 3c, 3d including all contained image diagnoses is summarized in a component ML (model logic) which is likewise connected to the user interface (see 3a, 3b).

Examples of examination results are shown in FIGS. 2 to 6, which are mapped onto a model of the overall body. Associated examination results may appear grouped on the lowest zoom stage (the grouping is based on the semantic annotations of the examination results, e.g. its anatomical localization). The type of visualization of the results (in this case as differently sized reference points R1 to R7) provides the user with an indication of the number of results per group.

Figure 2:
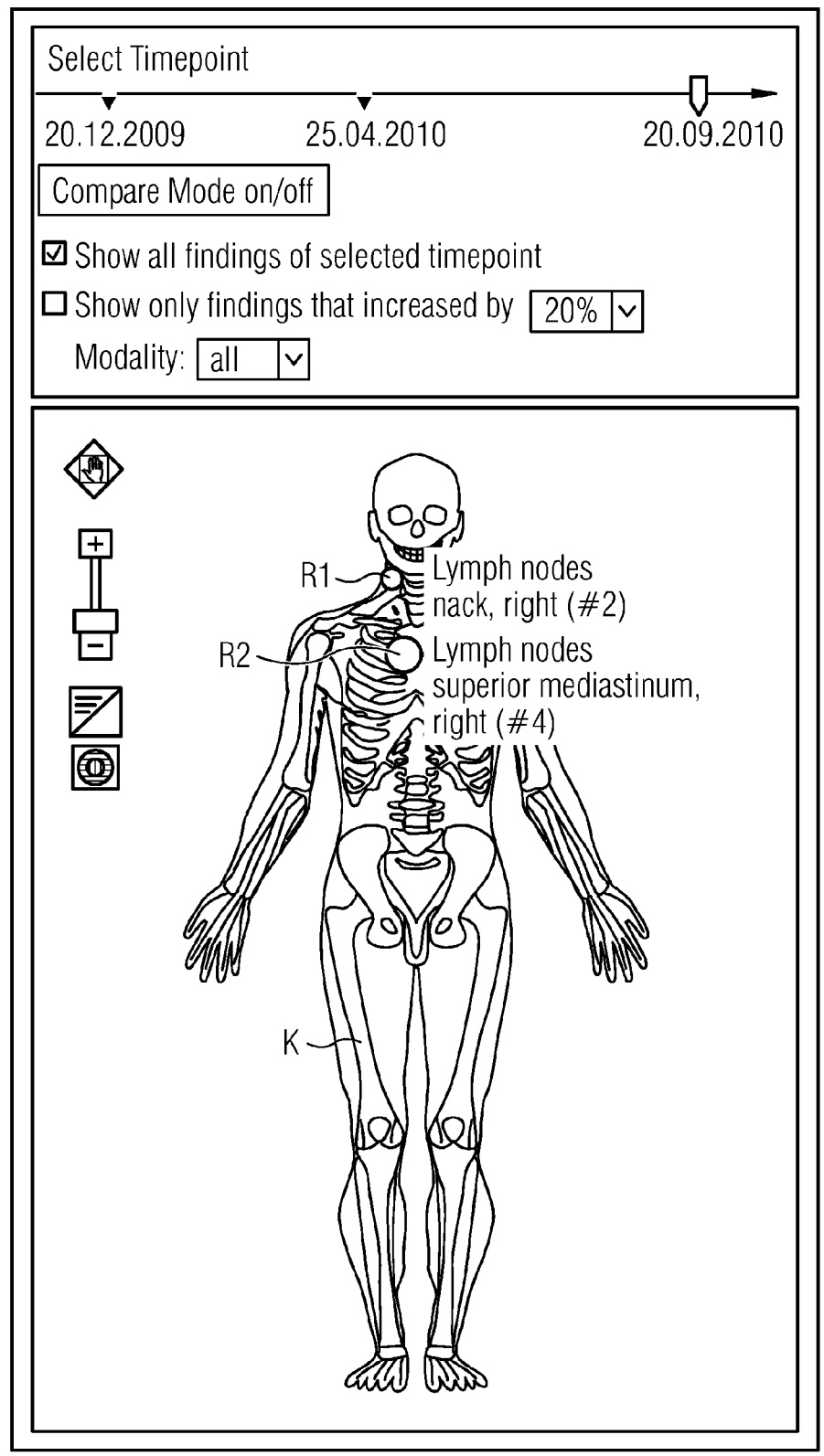
FIGS. 2 to 6 show example characteristics of the embodiments of the inventive representation.

Some textual information relating to the description of the examination results in the lowest zoom stage are shown by way of example in FIG. 2.

Figure 3:
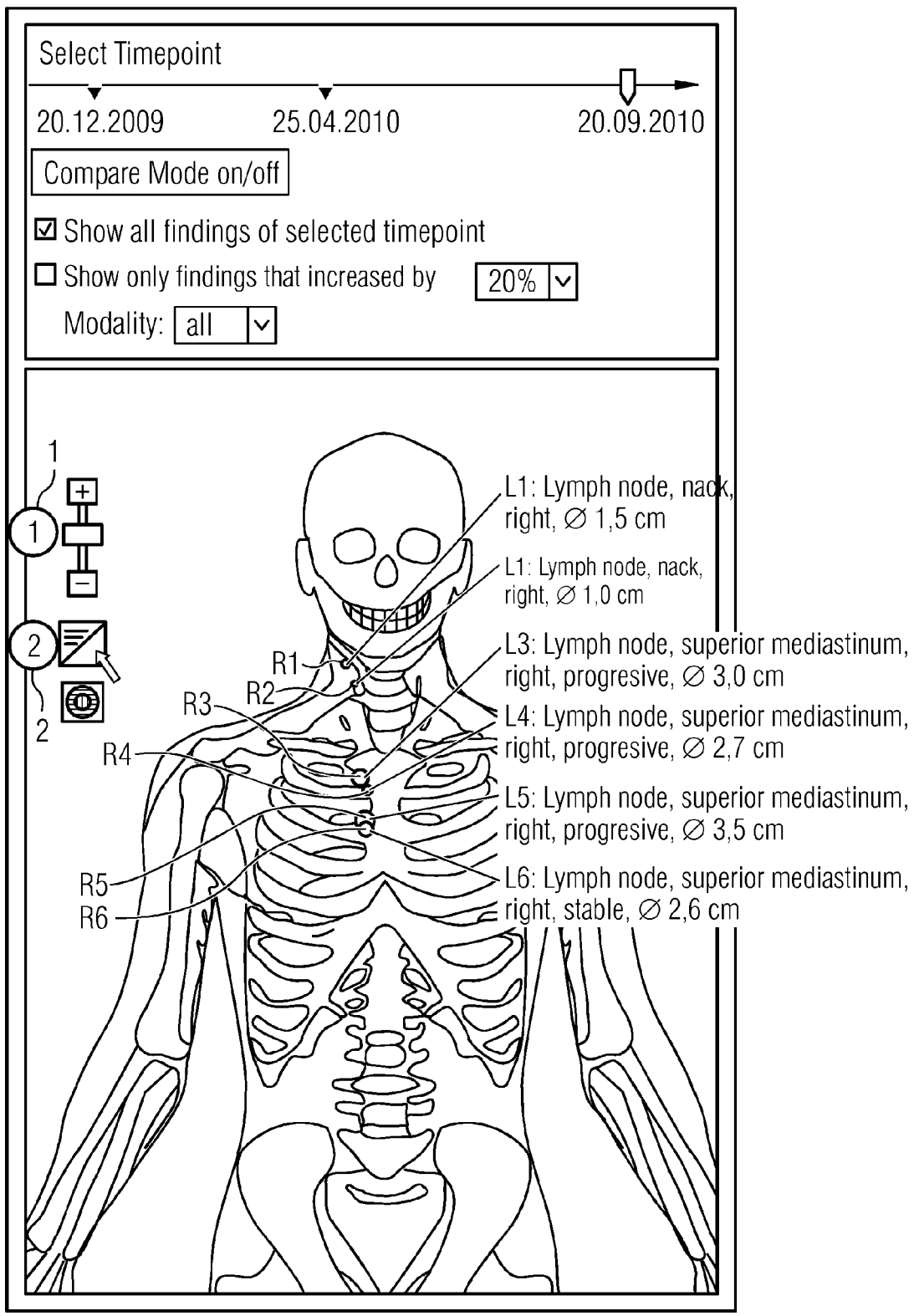

User interactions are shown in FIG. 3, which are characterized with 1 and 2:
 1. The user can change the zoom settings, so that more or less details relating to the examination results are shown.
 2. The user can switch the labels on and/or off.

Figure 4:
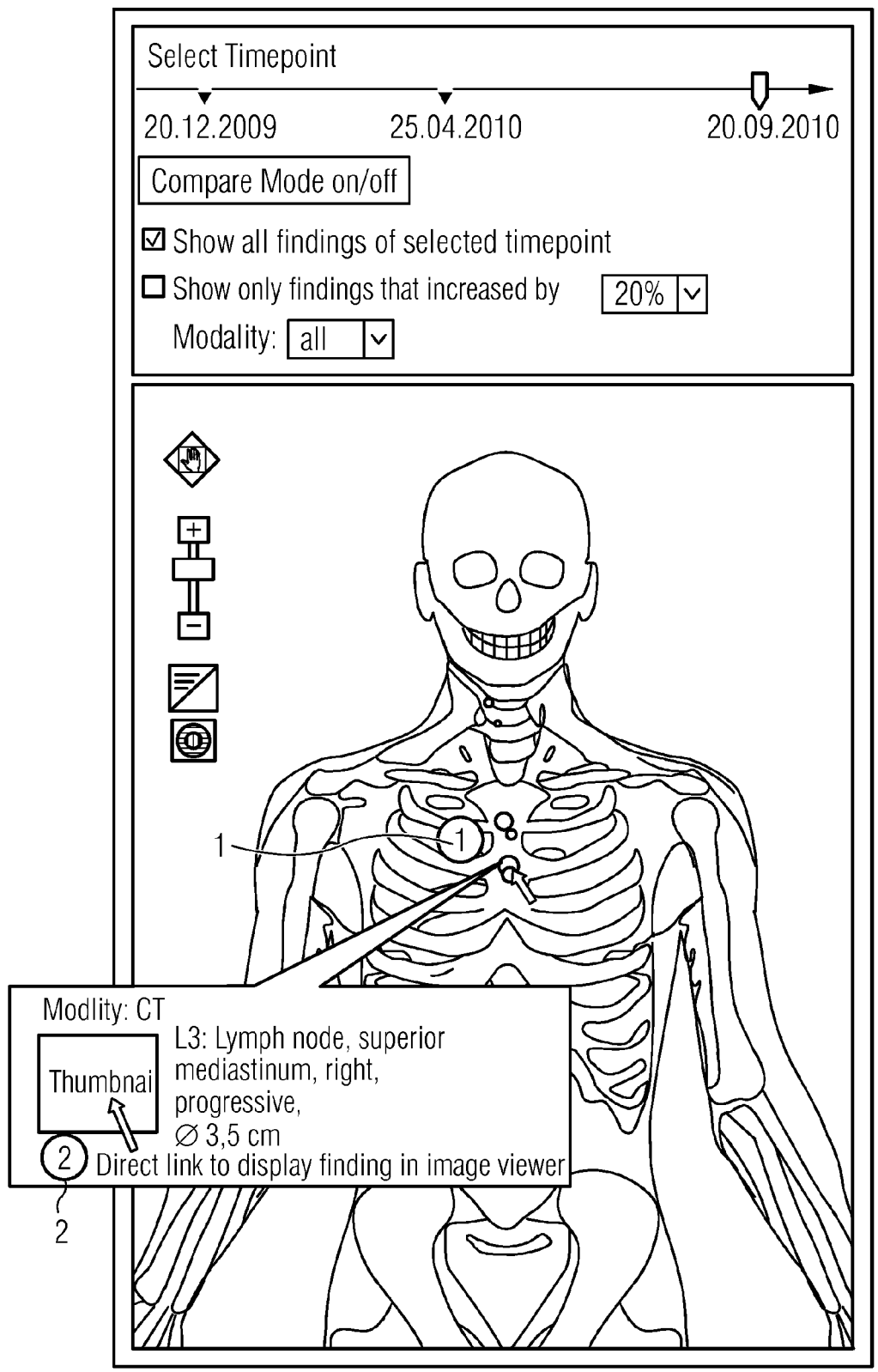

User interactions are shown in FIG. 4, which are identified with 1 and 2:
 1. If the user positions the mouse above an examination result, a preview pain appears with a detailed description of the result.
 2. In addition, if available, a preview image of the result can be shown. If the user clicks on this preview image, he navigates directly to this result in the original images.

Figure 5:
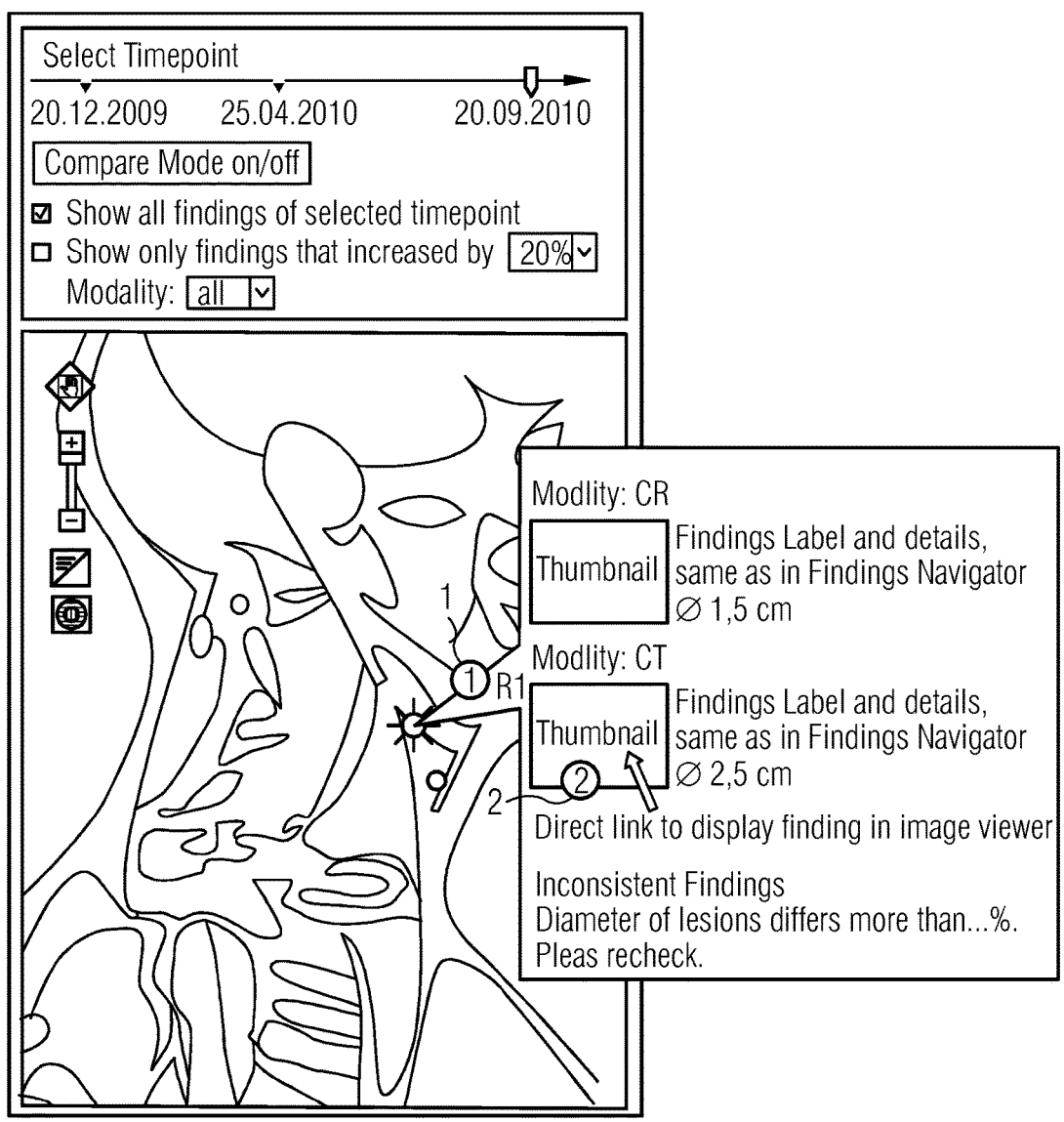

User interactions are shown in FIG. 5, which are identified with 1 and 2:
 1. If the system represents inconsistencies between examination results, this is shown visually directly in the model so that the attention of the user is directed to the inconsistency. If the user moves the mouse to the marked inconsistency, the system specifies the underlying detailed information.
 2. The user can jump directly to the results in the original images.

Figure 6:
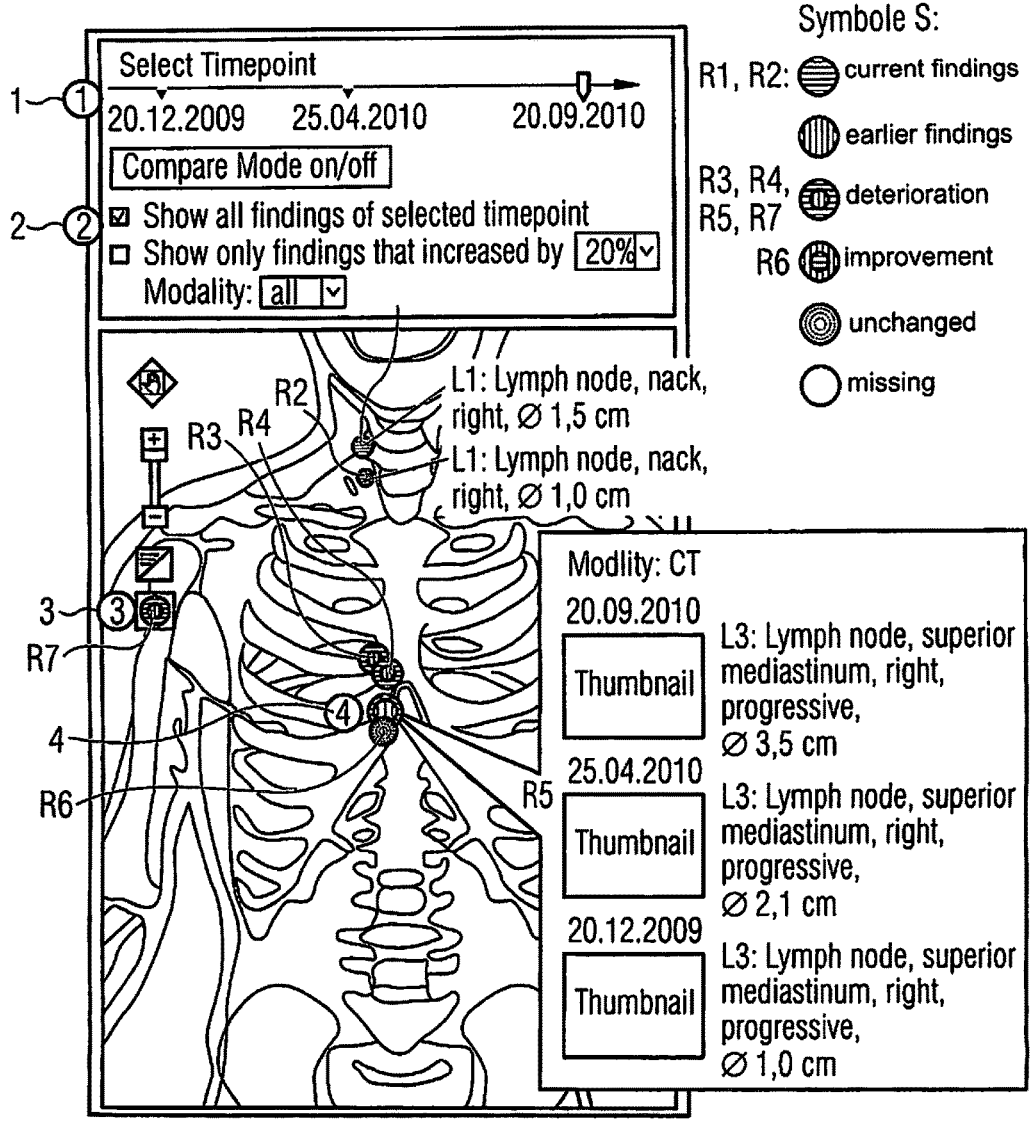

User interactions are shown in FIG. 6, which are identified with 1 to 4:
 1. The user can move to results of earlier examinations by way of a time bar. Furthermore, he/she can activate a comparison mode in order to select which time points are to be compared with one another.
 2. The user can select whether all results are shown or only those which correspond to certain criteria (e.g. change in size).
 3. Progress mode: if this mode is activated, the model visualizes the results in terms of their progress (worsening, improvement, no change etc.)
 4. The user can display a history at each examination result.

Furthermore, FIG. 6 shows the afore-cited progress mode having symbols S in color, which may have the following meaning, e.g.
red: (current finding)
green: (prior finding)
red-green: (got worse)
green-red: (got better)
brown: (unchanged)
white: (disappeared)

The following features, characteristics and advantages are favorable to an embodiment of the invention:

Instead of managing individual image diagnoses only in lists or unstructured diagnosis texts, these are shown in accordance with an embodiment of the invention in the context of a patient-specific whole body model and annotated with semantic metadata. This enables registration of the image data on the model which is to assign image diagnoses to the correct anatomical structures, wherein consistency tests can be implemented between data records of different modalities and redundant diagnoses can be unified. The model enables an efficient navigation across various body regions and organs including continuous zooming, extensive filtering of the image diagnoses (e.g. individual diagnoses relating to the vascular system and/or only individual diagnoses of specifically severe and/or worsening individual diagnoses and/or restricted to specific imaging methods or procedures). The representation of various detailed stages, schematic representation of changes to the image diagnoses by means of special symbols is possible (newly occurring image diagnoses, image diagnoses which indicate an improvement or worsening, image diagnoses which have no correspondence in terms of current examination).

One development is a possibility of obtaining a quick overview of changes, since these can indicate a change in the state of health of the patient but may also be an indication that the radiologist has overseen an image diagnosis relating to a time instant or estimated/measured the same differently. The temporal progress can therefore not only be represented by special symbols, but instead also by the (automatically or manually triggered) continuous display of the model relating to the available time instants with continuous zoom and filter settings. A film of the changes over time can result with a quick sequence of these steps.

The abstract, interactive representation of the diagnoses in relation to the anatomy of the patient enables, in the manner described above, an improved, comprehensive understanding of the clinical picture, since important context information is made public with each diagnosis.

Furthermore, this approach enables the elimination of separate schematic representations of individual organs for the qualitative illustration when localizing the diagnoses. The model can be interactively or automatically reduced in terms of its information density, as described above and only the relevant parts are shown.

Accordingly rotated and enlarged, an equivalent, simplified and qualitatively important visualization of the diagnoses can be achieved. Redundant development effort can be saved in this way which reduces the complexity, and renders simpler future visualizations.

Furthermore, reuse is possible in accordance with embodiment of the invention. This brings about a recognition and learning effect in the case of users of the system and results over time in a more efficient operation.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

A algorithms/services
B user interface
D data management
E diagnosis editor
I image interpretation
K body model
ML model logic
REGB registration of image with model K
REGM registration of text with model K
R1 to R7 reference points and/or positions e.g. R1: lymph nodes, neck, right, S symbols in color, e.g. in red, green, red-green, green-red, brown, white
1, 2, 3, 4 interactions
1a, 1b classical registration algorithms
2a, 2b registration on the body model
3a, 3b storage and/or charging
3c, 3d communication between user interface and model logic

What is claimed is:

1. A method for computer-assisted structuring of medical examination data, comprising:
   providing at least one medical examination data record, including
   (i) patient-specific diagnostic data described at least one of textually and symbolically, and
   (ii) at least two images including different types of scan data from a group including computed tomography, magnetic resonance tomography, positron emission tomography, x-ray and ultrasound scan data;
   providing at least one body model image, the at least one body model image representing a body model which matches the at least one medical examination data record;
   assigning at least one position in the at least one body model image to the at least one medical examination data record, the at least one position corresponding to a physiological area of interest of the at least one medical examination data record;
   generating at least one interface element at the at least one position such that the medical examination data record can be interacted with and viewed by way of a user interface;
   permitting a preview of a first image of the at least two images over the at least one position based on an action from a user on the at least one position by displaying the preview of the first image in a preview window, the preview window being superimposed on the at least one body model image, the preview of the first image linking to the first image; and
   providing a status identifier at the at least one position, the status identifier indicates progress of a pathological condition associated with the at least one medical examination data record.

2. The method of claim 1, wherein a change in pathological structure compared with a preceding, earlier evaluation of the at least one medical examination data record is determined, annotated and made known for interaction by way of the user interface.

3. The method of claim 2, wherein a determined position of the pathological structure, the determined change in the pathological structure and determined properties of the pathological structure are combined and shown in a structured form.

4. The method of claim 3, wherein inconsistencies are exposed with the aid of the structured form.

5. The method of claim 3, wherein redundancies are exposed with the aid of the structured form.

6. The method of claim 1, wherein the status identifier corresponds to a selected timepoint of the at least one medical examination data record.

7. The method of claim 6, wherein the status identifier indicates one of current findings, earlier findings, deterioration, improvement, unchanged and missing.

8. The method of claim 1, wherein the at least one position is displayed on a display apparatus.

9. The method of claim 1, wherein semantic meta data are annotated on the at least one position.

10. The method of claim 1, wherein permitting the preview of the first image includes displaying a textual description of the at least one medical examination data record associated with the at least one position in the preview window, and displaying a preview image of the first image in the preview window.

11. An arrangement for computer-assisted structuring of medical examination data, comprising:
   a processor configured to,
   provide at least one medical examination data record, including
   (i) patient-specific diagnostic data described at least one of textually and symbolically, and
   (ii) at least two images including different types of scan data from a group including computed tomography, magnetic resonance tomography, positron emission tomography, x-ray and ultrasound scan data,
   provide at least one body model image, the at least one body model image representing a body model which matches the at least one medical examination data record,
   assign at least one position in the at least one body model image to the at least one medical examination data record, the at least one position corresponding to a physiological area of interest of the at least one medical examination data record,
   generate at least one interface element at the at least one position such that the medical examination data record can be interacted with and viewed by way of a user interface,
   permit a preview of a first image of the at least two images over the at least one position based on an action from a user on the at least one position by displaying the preview of the first image in a preview window, the preview window being superimposed on the at least one body model image, the preview of the first image linking to the first image, and
   provide a status identifier at the at least one position, the status identifier indicates progress of a pathological condition associated with the at least one medical examination data record.

12. The arrangement of claim 11, wherein the processor is further configured to determine, annotate and make known of a change in pathological structure compared with a preceding, earlier evaluation of the at least one medical examination data record.

13. The arrangement of claim 12, wherein the processor is further configured to combine a determined position of the pathological structure, the determined change in the pathological structure and determined properties of the pathological structure in a structured form.

14. The arrangement of claim 13, wherein the processor is further configured to at least one of expose and making known inconsistencies with the aid of the structured form.

15. The arrangement of claim 13, wherein the processor is further configured to at least one of expose and eliminate redundancies with the aid of the structured form.

16. The arrangement of claim 11, wherein the processor is further configured to represent the at least one position in the at least one body model image on a display apparatus.

17. The arrangement of claim 11, wherein the processor is further configured to annotate semantic meta data at the at least one position.

18. The arrangement of claim 11, wherein the processor is further configured to permit the preview of the first image including displaying a textual description of the at least one medical examination data record associated with the at least one position in the preview window, and displaying a preview image of the first image in the preview window.

19. A non-transitory computer-readable medium storing instructions that, when executed by a processor, cause the processor to:
  provide at least one medical examination data record, including
    (i) patient-specific diagnostic data described at least one of textually and symbolically, and
    (ii) at least two images including different types of scan data from a group including computed tomography, magnetic resonance tomography, positron emission tomography, x-ray and ultrasound scan data;
  providing at least one body model image, the at least one body model image representing a body model which matches the at least one medical examination data record;
  assigning at least one position in the at least one body model image to the at least one medical examination data record, the at least one position corresponding to a physiological area of interest of the at least one medical examination data record;
  generating at least one interface element at the at least one position such that the medical examination data record can be interacted with and viewed by way of a user interface;
  permitting a preview of a first image of the at least two images over the at least one position based on an action from a user on the at least one position by displaying the preview of the first image in a preview window, the preview window being superimposed on the at least one body model image, the preview of the first image linking to the first image; and
  providing a status identifier at the at least one position, the status identifier indicates progress of a pathological condition associated with the at least one medical examination data record.

20. The non-transitory computer-readable medium of claim 19, wherein the instructions further cause the processor to permit the preview of the first image including displaying a textual description of the at least one medical examination data record associated with the at least one position in the preview window, and displaying a preview image of the first image in the preview window.

* * * * *